(12) United States Patent
Nickel et al.

(10) Patent No.: US 6,232,327 B1
(45) Date of Patent: May 15, 2001

(54) INDOLYL-3-GLYOXYLIC ACID DERIVATIVES HAVING ANTITUMOR ACTION

(75) Inventors: Bernd Nickel, Mühltal; Istvan Szelenyi, Schwaig; Jürgen Schmidt, Uhldingen Mühlhofen; Peter Emig, Bruchköbel; Dietmar Reichert, Eschau; Eckhard Günther, Maintal; Kay Brune, Marloffstein, all of (DE)

(73) Assignee: Asta Medica Aktiengesellschaft, Dresden (DE)

( * ) Notice: Subject to any disclaimer, the term of this patent is extended or adjusted under 35 U.S.C. 154(b) by 0 days.

(21) Appl. No.: 09/285,058

(22) Filed: Apr. 2, 1999

(30) Foreign Application Priority Data

Apr. 2, 1998 (DE) ............................................ 198 14 838

(51) Int. Cl.$^7$ ...................... A61K 31/435; A61K 31/475; C07D 209/04; C07D 213/04
(52) U.S. Cl. ...................... 514/337; 546/278.1; 546/256
(58) Field of Search ...................... 514/337; 546/278.1, 546/256

(56) References Cited

U.S. PATENT DOCUMENTS 5,405,864 * 4/1995 Broka et al. ............................ 514/415

FOREIGN PATENT DOCUMENTS

2315989 * 4/1973 (DE).
98/09946 * 3/1998 (WO).

OTHER PUBLICATIONS

Caplu 1969:37598; Podwinski Bohdan , Synthesis of some 5–benzyl . . . , RN # 21421–40–9, 1966.*
Caplus An Apr. 1999:708761, Hofgen Norbert et al , RN 247584–34–5.*

* cited by examiner

*Primary Examiner*—Alan L. Rotman
*Assistant Examiner*—Rita Desai

(57) ABSTRACT

The invention relates to the use of N-substituted indole-3-glyoxylamides of the general formula I as antitumor agents Formula 1 and to a pharmaceutical composition having antitumor action, characterized in that it contains at least one of the compounds of the general formula 1, if appropriate also in the form of the physiologically tolerable acid addition salts or N-oxides. Furthermore, the invention also includes antitumor agents comprising as active compound one or more N-substituted indole-3-glyoxylamides according to the general formula 1 and, if appropriate, their physiologically tolerable acid addition salts and, if possible, N-oxides and a pharmaceutically utilizable carrier and/or diluent or auxiliary substance in the form of tablets, coated tablets, capsules, solutions for infusion or ampoules, suppositories, patches, powder preparations which can be employed by inhalation, suspensions, creams and ointments.

5 Claims, 2 Drawing Sheets

Murine leucemia L 1210: D 24851 i.p.

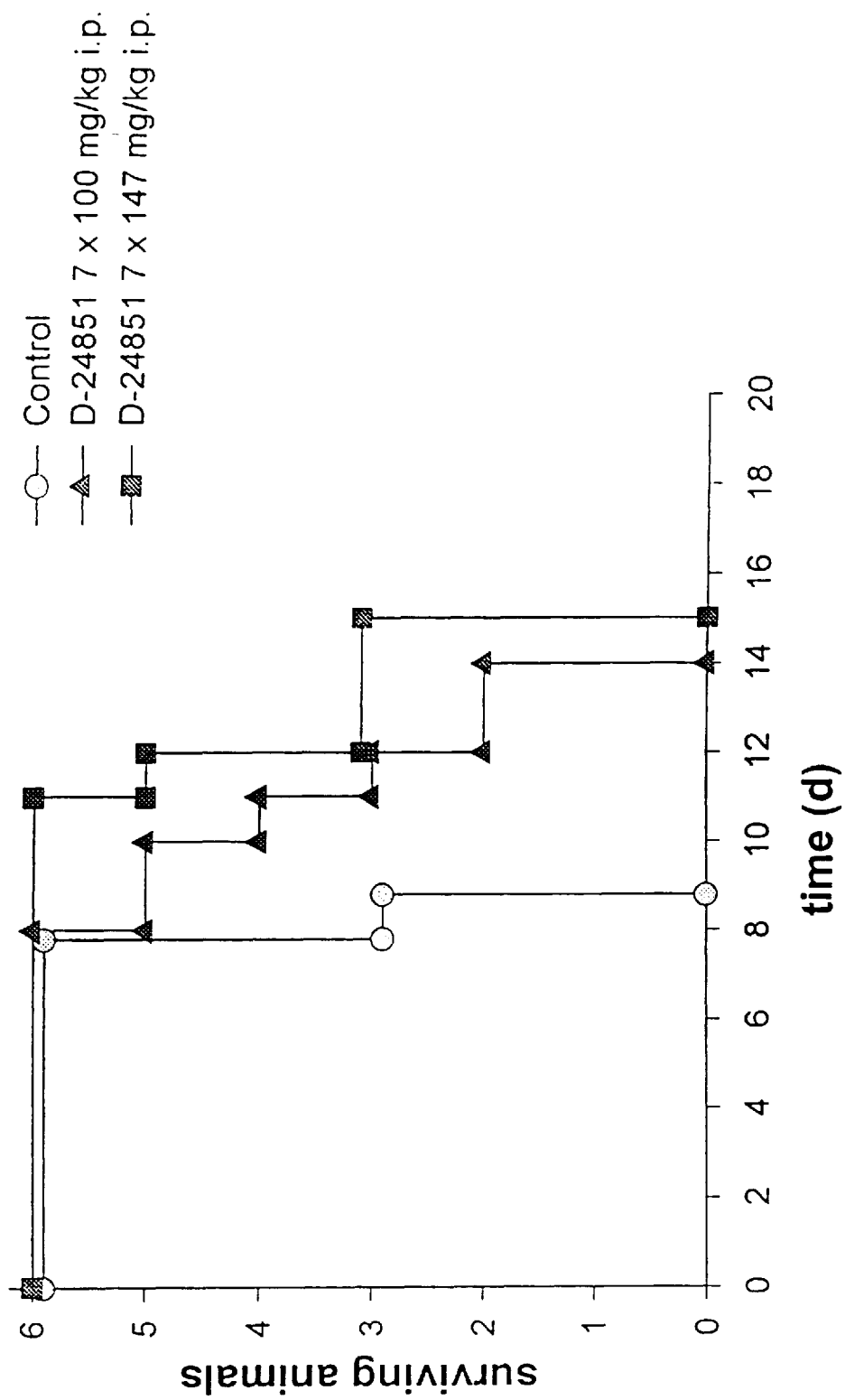
Figure 1a Murine leucemia L 1210: D 24851 i.p.

INDOLYL-3-GLYOXYLIC ACID DERIVATIVES HAVING ANTITUMOR ACTION

BACKGROUND OF THE INVENTION

1. Field of the Invention

Indole-3-glyoxylamides have a variety of uses as pharmacodynamically active compounds and as synthetic building blocks in pharmaceutical chemistry.

2. Background Information

In the patent application Neth. Appl. 6502481, compounds are described which have an anti-inflammatory and antipyretic activity profile and analgesic activity.

In the British Application GB-B 1 028 812, derivatives of indolyl-3-glyoxylic acid and their amides are used as analgesic, anticonvulsant and β-adrenergic compounds.

G. Domschke et al. (Ber. 94, 2353 (1961)) describes [sic] 3-indolylglyoxylamides which are not characterized pharmacologically.

E. Walton reports in *J. Med. Chem*, 11, 1252 (1968) on indolyl-3-glyoxylic acid derivatives which have an inhibitory action on glycerophosphate dehydrogenase and lactate dehydrogenase.

In the European Patent Specification EP 675110, 1H-indole-3-glyoxylamides are described which are profiled as sPLA2 inhibitors and are used in the treatment of septic shock, in pancreatitis and in the treatment of allergic rhinitis and rheumatoid arthritis.

The aim of the present invention is to make available N-substituted indole-3-glyoxylamides which have an antitumor action and thus to enrich the available pharmaceutical wealth.

The compounds mentioned have already been disclosed as medicaments having antiasthmatic, antiallergic and immunosuppressant/immunomodulating action in DE-A 19636150 A1.

SUMMARY OF THE INVENTION

The invention therefore relates to the use of N-substituted indole-3-glyoxylamides of the general formula 1 for the production of antitumor agents, antitumor agents having a content of active substance according to formula 1 and their use for the treatment of oncoses.

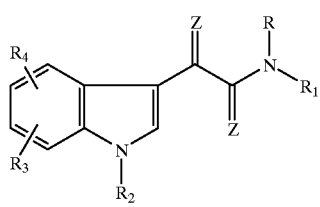

Formula 1 where the radicals R, $R_1$, $R_2$, $R_3$, $R_4$ and Z have the following meaning:

R=hydrogen, $(C_1-C_6)$-alkyl, where the alkyl group can be mono- or polysubstituted by the phenyl ring and this phenyl ring for its part can be mono- or polysubstituted by halogen, $(C_1-C_6)$-alkyl, $(C_3-C_7)$-cycloalkyl, by carboxyl groups, carboxyl groups esterified with $C_1-C_6$-alkanols, trifluoromethyl groups, hydroxyl groups, methoxy groups, ethoxy groups, benzyloxy groups and by a benzyl group which is mono- or polysubstituted in the phenyl moiety by $(C_1-C_6)$-alkyl groups, halogen atoms or trifluoromethyl groups, R is further the benzyloxycarbonyl group (Z group) and the tertiary-butoxycarbonyl radical (BOC radical), furthermore the acetyl group.

$R_1$ can be the phenyl ring, which is mono- or polysubstituted by $(C_1-C_6)$-alkyl, $(C_1-C_6)$-alkoxy, cyano, halogen, trifluoromethyl, hydroxyl, benzyloxy, nitro, amino, $(C_1-C_6)$-alkylamino, $(C_1-C_6)$-alkoxycarbonylamino and by the carboxyl group or by the carboxyl group esterified with $C_1-C_6$-alkanols, or can be a pyridine structure of the formula 2 and its N-oxide [sic]

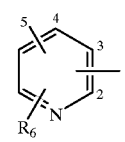

Formula 2 and its N-oxide, where the pyridine structure is alternatively bonded to the ring carbon atoms 2, 3 and 4 and can be substituted by the substituents $R_5$ and $R_6$. The radicals $R_5$ and $R_6$ can be identical or different and have the meaning $(C_1-C_6)$-alkyl and the meaning $(C_3-C_7)$-cycloalkyl, $(C_1-C_6)$-alkoxy, nitro, amino, hydroxyl, halogen and trifluoromethyl and further are the ethoxycarbonylamino radical and the group carboxyalkyloxy in which the alkyl group can have 1–4 C atoms.

$R_1$ can further be a 2- or 4-pyrimidinyl heterocycle, where the 2-pyrimidinyl ring can be mono- or polysubstituted by the methyl group, furthermore are [sic] the 2-, 3-, and 4- and 8-quinolyl structure substituted by $(C_1-C_6)$-alkyl, halogen, the nitro group, the amino group and the $(C_1-C_6)$-alkylamino radical, are [sic] a 2-, 3- and [sic] 4-quinolylmethyl group, where the ring carbons of the pyridylmethyl radical of the quinolyl group and of the quinolylmethyl radical can be substituted by $(C_1-C_6)$-alkyl, $(C_1-C_6)$-alkoxy, nitro, amino and $(C_1-C_6)$-alkoxycarbonylamino.

$R_1$ in the case in which R=hydrogen, the methyl or benzyl group and the benzyloxycarbonyl radical (Z radical), the tert-butoxycarbonyl radical (BOC radical) and the acetyl group, can furthermore be the following radicals: $CH_2COOH$; $—CH(CH_3)—COOH$; $—(CH_3)_2—CH—(CH_2)_2—CH—COO—$; $H_3C—H_2C—CH(CH_3)—CH(COOH)—$; $HO—H_2C—CH(COOH)—$; phenyl—$CH_2—CH(COOH)—$; (4-imidazolyl)—$CH_2—CH(COOH)—$; $HN=C(NH_2)—NH—(CH_2)_3—CH(COOH)—$; $H_2N—(CH_2)_4—CH(COOH)—$; $H_2N—CO—CH_2—CH—(COOH)—$; $HOOC—(CH_2)_2—CH(COOH)—$;

$R_1$ in the case in which R is hydrogen, the Z group, the BOC radical, the acetyl or the benzyl group, can furthermore be the acid radical of a natural or unnatural amino acid, e.g. the α-glycyl, the α-sarcosyl, the α-alanyl, the α-leucyl, the α-isoleucyl, the α-seryl, the α-phenylalanyl, the α-histidyl, the α-prolyl, the α-arginyl, the α-lysyl, the α-asparagyl and the α-glutamyl radical, where the amino groups of the respective amino acids can be present unprotected or can be protected. A possible protective group of the amino function is the carbobenzoxy radical (Z radical) and the tert-butoxycarbonyl radical (BOC radical) as well as the acetyl group. In the case of the asparagyl and glutamyl radical claimed for $R_1$, the second, unbonded carboxyl group is present as a free carboxyl group or in the form of an ester with $C_1$–$C_6$-alkanols, e.g. as a methyl, ethyl or as a tert-butyl ester.

Furthermore, $R_1$ can be the allylaminocarbonyl-2-methylprop-1-yl group.

R and $R_1$ can further form, together with the nitrogen atom to which they are bonded, a piperazine ring of the formula III or a homopiperazine ring, provided $R_1$ is an aminoalkylene group, in which Formula 3

$R_7$ is an alkyl radical, is a phenyl ring which can be mono- or polysubstituted by ($C_1$–$C_6$)-alkyl, ($C_1$–$C_6$)-alkoxy, halogen, the nitro group, the amino function and by the ($C_1$–$C_6$)-alkylamino group. $R_7$ is furthermore the benzhydryl group and the bis-p-fluorobenzylhydryl [sic] group.

$R_2$ can be hydrogen and the ($C_1$–$C_6$)-alkyl group, where the alkyl group is mono- or polysubstituted by halogen and phenyl, which for its part can be mono- or polysubstituted by halogen, ($C_1$–$C_6$)-alkyl, ($C_3$–$C_7$)-cycloalkyl, carboxyl groups, carboxyl groups esterified with $C_1$–$C_6$-alkanols, trifluoromethyl groups, hydroxyl groups, methoxy groups, ethoxy groups or benzyloxy groups. The ($C_1$–$C_6$)-alkyl group counting as $R_2$ can further be substituted by the 2-quinolyl group and the 2-, 3- and 4-pyridyl structure, which can both in each case be mono- or polysubstituted by halogen, ($C_1$–$C_4$)-alkyl groups or ($C_1$–$C_4$)-alkoxy groups. $R_2$ is further the aroyl radical, where the aryl moiety on which this radical is based is the phenyl ring, which can be mono- or polysubstituted by halogen, ($C_1$–$C_6$)-alkyl, ($C_3$–$C_7$)-cycloalkyl, carboxyl groups, carboxyl groups esterified with $C_1$–$C_6$-alkanols, trifluoromethyl groups, hydroxyl groups, methoxy groups, ethoxy groups or benzyloxy groups.

$R_3$ and $R_4$ can be identical or different and are hydrogen, ($C_1$–$C_6$)-alkyl, ($C_3$–$C_7$)-cycloalkyl, ($C_1$–$C_6$)-alkanoyl, ($C_1$–$C_6$)-alkoxy, halogen and benzyloxy. $R_3$ and $R_4$ can furthermore be the nitro group, the amino group, the ($C_1$–$C_4$)-mono or dialkyl-substituted amino group, and the ($C_1$–$C_6$)-alkoxycarbonylamino function or ($C_1$–$C_6$)-alkoxycarbonylamino-($C_1$–$C_6$)-alkyl function.

Z is O and S.

The designation alkyl, alkanol, alkoxy or alkylamino group for the radicals R, $R_1$, $R_2$, $R_3$, $R_4$, $R_5$, $R_6$, $R_7$ is normally understood as meaning both "straight-chain" and "branched" alkyl groups, where "straight-chain alkyl groups can be, for example, radicals such as methyl, ethyl, n-propyl, n-butyl, n-pentyl, n-hexyl and "branched alkyl groups" designate, for example, radicals such as isopropyl or tert-butyl. "Cycloalkyl" is understood as meaning radicals such as, for example, cyclopropyl, cyclobutyl, cyclopentyl, cyclohexyl or cycloheptyl.

The designation "halogen" represents fluorine, chlorine, bromine or iodine. The designation "alkoxy group" represents radicals such as, for example, methoxy, ethoxy, propoxy, butoxy, isopropoxy, isobutoxy or pentoxy.

The compounds can also be employed as acid addition salts, for example as salts of mineral acids, such as, for example, hydrochloric acid, sulfuric acid, phosphoric acid, salts of organic acids, such as, for example, acetic acid, lactic acid, malonic acid, maleic acid, fumaric acid, gluconic acid, glucuronic acid, citric acid, embonic acid, methanesulfonic acid, trifluoroacetic acid, succinic acid and 2-hydroxyethanesulfonic acid.

Both the compounds of the formula 1 and their salts are biologically active.

The compounds of the formula 1 can be administered in free form or as salts with physiologically tolerable acids.

Administration can be performed orally, parenterally, intravenously, transdermally or by inhalation.

The invention furthermore relates to pharmaceutical preparations which contain at least one of the compounds of the formula 1 or their salts with physiologically tolerable inorganic or organic acids and, if appropriate, pharmaceutically utilizable excipients and/or diluents or auxiliaries.

Suitable administration forms are, for example, tablets, coated tablets, capsules, solutions for infusion or ampoules, suppositories, patches, powder preparations which can be employed by inhalation, suspensions, creams and ointments.

The processes for the production of the compounds according to the invention are described in the following reaction schemes 1 and 2 and in general procedures. All compounds can be prepared as described or analogously.

The compounds of the general formula 1 with Z=O, $R_1$=aryl, aralkyl, heteroaryl and heteroaralkyl and $R_2$=alkyl, aralkyl and heteroaralkyl are obtainable according to the following Scheme 1:

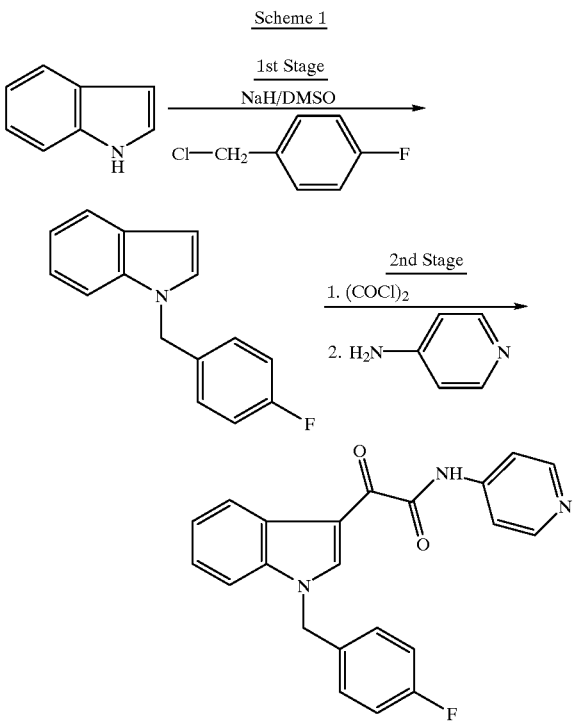

1st Stage

The indol derivative, which can be unsubstituted or monosubstituted or polysubstituted on C-2 or in the phenyl structure, is dissolved in a protic, dipolar aprotic or nonpolar organic solvent, such as, for example, isopropanol, tetrahydrofuran, dimethyl sulfoxide, dimethylformamide, dimethylacetamide, N-methylpyrrolidone, dioxane, toluene or methylene chloride and added dropwise to a suspension of a base prepared in a three-necked flask under an $N_2$ atmosphere or employed in a molar amount or in excess, such as, for example, sodium hydride, powdered potassium hydroxide, potassium tert-butoxide, dimethylaminopyridine or sodium amide, in a suitable solvent. Then the desired alkyl, aralkyl or heteroaralkyl halide, for example, is added, if appropriate with addition of a catalyst, such as, for example, copper and the mixture is allowed to react for some time, for example for 30 minutes to 12 hours, and the temperature is maintained within a range from 0° C. to 120° C., preferably between 30° C. to [sic] 80° C., particularly between 50° C. and 65° C. After completion of the reaction, the reaction mixture is added to water, the solution is extracted, e.g. with diethyl ether, dichloromethane, chloroform, methyl tert-butyl ether or tetrahydrofuran, and the organic phase obtained in each case is dried with anhydrous sodium sulfate. The organic phase is concentrated in vacuo, the residue which remains is crystallized by trituration or the oily residue is purified by recrystallization, distillation or by column or flash chromatography on silica gel or alumina. The eluent used is, for example, a mixture of dichloromethane and diethyl ether in the ratio 8:2 (vol/vol) or a mixture of dichloromethane and ethanol in the ratio 9:1 (vol/vol).

2nd Stage

The N-substituted indol obtained according to the above procedure of the 1st Stage is dissolved under a nitrogen atmosphere in an aprotic or nonpolar organic solvent, such as, for example, diethyl ether, methyl tert-butyl ether, tetrahydrofuran, dioxane, toluene, xylene, methylene chloride or chloroform and added to a solution prepared under a nitrogen atmosphere of a monomolar up to 60% excess amount of oxalyl chloride in an aprotic or nonpolar solvent, such as, for example, in diethyl ether, methyl tert-butyl ether, tetrahydrofuran, dioxane, toluene, xylene, methylene chloride, the temperature being kept between −5° C. and 20° C. The reaction solution is then heated at a temperature between 10° C. and 130° C., preferably between 20° C. and 80° C., particularly between 30° C. and 50° C., for a period of 30 minutes to 5 hours and the solvent is then evaporated. The residue of the "indolyl-3-glyoxyloyl chloride" formed in this manner which remains is dissolved in an aprotic solvent such as, for example, tetrahydrofuran, dioxane, diethyl ether, toluene or alternatively in a dipolar aprotic solvent, such as, for example, dimethylformamide, dimethylacetamide or dimethyl sulfoxide, cooled to a temperature between 10° C. and −15° C., preferably between −5° C. and 0° C., and treated in the presence of an acid scavenger with a solution of the primary or secondary amine in a diluent. Possible diluents are the solvents used above for dissolving the indolyl-3-glyoxyloyl chloride. Acid scavengers used are triethylamine, pyridine, dimethylaminopyridine, basic ion exchanger, sodium carbonate, potassium carbonate, powdered potassium hydroxide and excess primary or secondary amine employed for the reaction. The reaction takes place at a temperature from 0° C. to 120° C., preferably at 20–80° C., particularly between 40° C. and 60° C. After a reaction time of 1–3 hours and standing at room temperature for 24 hours, the hydrochloride of the acid scavenger is filtered, the filtrate is concentrated in vacuo and the residue is recrystallized from an organic solvent or purified by column chromatography on silica gel or alumina. Eluents used are, for example, a mixture of dichloromethane and ethanol (95:5, vol/vol).

BRIEF DESCRIPTION OF THE DRAWINGS

FIG. 1a: Intraperitoneal administration of Murine Leukemia L 1210:D24851

DETAILED DESCRIPTION OF THE INVENTION

Figure 1B:
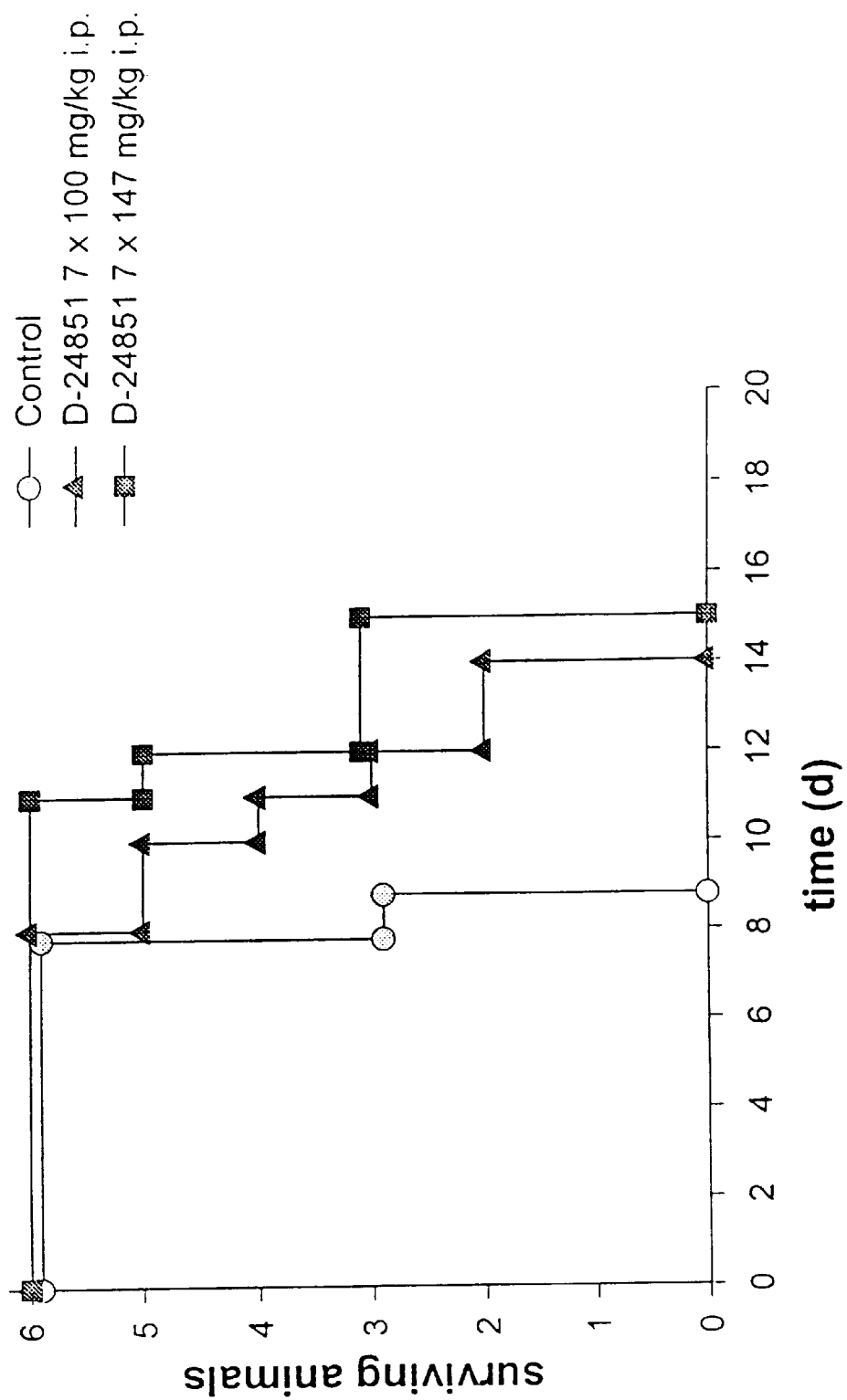
FIG. 1b: Oral administration of Murine Leukemia L 1210:D24851

According to this general procedure for Stages 1 and 2, on which synthesis scheme 1 is based, the following compounds were synthesized which are evident from the following tabulated list detailing the respective chemical name. In Tables 1a–j on pages A–J, the structures of these compounds and their melting points can be seen from the general formula 1 and the substituents $R_1$–$R_4$ and Z:

EXAMPLE 1

N-(Pyridin-4-yl)-[1-(4-fluorobenzyl)indol-3-yl}glyoxylamide (D 24241)

1st Stage 1-(4-Fluorobenzyl)indole

A solution of 11.72 g (0.1 mol) of indol in 50 ml of dimethyl sulfoxide is added to a mixture of 2.64 g of sodium hydride (0.11 mol, mineral oil suspension) in 100 ml of dimethyl sulfoxide. The mixture is heated at 60° C. for 1.5 hours, then allowed to cool and 15.9 g (0.11 mol) of 4-fluorobenzyl chloride are added dropwise. The solution is warmed to 60° C., allowed to stand overnight and then poured into 400 ml of water with stirring. The mixture is extracted a number of times with a total of 150 ml of methylene chloride, the organic phase is dried using anhydrous sodium sulfate, filtered and the filtrate is concentrated in vacuo. The residue is distilled in a high vacuum: 21.0 g (96% of theory) b.p. (0.5 mm): 140° C.

2nd Stage

N-(Pyridin-4-yl)-[1-(4-fluorobenzyl)indol-3-yl] glyoxylamide (D 24241)

A solution of 4.75 g (21.1 mmol) of 1-(4-fluorobenzyl) indol in 25 ml of ether is added dropwise at 0° C. and under $N_2$ to a solution of 2.25 ml of oxalyl chloride in 25 ml of ether. The mixture is heated to reflux for 2 hours and the solvent is then evaporated. 50 ml of tetrahydrofuran were then added to the residue, the solution was cooled to −5° C. and treated dropwise with a solution of 4.66 g (49.5 mmol) of 4-aminopyridine in 200 ml of THF. The mixture is heated to reflux for 3 hours and allowed to stand at room temperature overnight. The 4-aminopyridine hydrochloride is filtered off with suction, the precipitate is washed with THF, the filtrate is concentrated in vacuo and the residue is recrystallized from ethyl acetate.

Yield: 7.09 g (90% of theory)

Melting point: 225–226° C.

Elemental analysis:

| | | | |
|---|---|---|---|
| ber. | C 70,77 | H 4.32 | N 11.25 |
| gef. | C 71.09 | H 4.36 | N 11.26 |

EXAMPLE 2

D 24242 N-(Pyridin-4-yl)-(1-methylindol-3-yl)
glyoxylamide

EXAMPLE 3

D 24834 N-(Pyridin-3-yl)-[1-(4-fluorobenzyl)indol-3-yl]glyoxylamide

EXAMPLE 4

D 24835 N-(Pyridin-3-yl)-(1-benzylindol-3-yl)
glyoxylamide

EXAMPLE 5

D 24836 N-(Pyridin-3-yl)-[1-(2-chlorobenzyl)indol-3-yl]glyoxylamide

EXAMPLE 6

D 24840 N-(4-Fluorophenyl)-[1-(4-fluorobenzyl)
indol-3-yl]glyoxylamide

EXAMPLE 7

D 24941 N-(4-Nitrophenyl)-[1-(4-fluorobenzyl)
indol-3-yl]glyoxylamide

EXAMPLE 8

D 24842 N-(2-Chloropyridin-3-yl)-[1-(4-fluorobenzyl)indol-3-yl]glyoxylamide

EXAMPLE 9

D 24843 N-(Pyridin-4-yl)-(1-benzylindol-3-yl)
glyoxylamide

EXAMPLE 10

D 24848 N-(Pyridin-4-yl)-[1-(3-pyridylmethyl)
indol-3-yl]glyoxylamide

EXAMPLE 11

D 24849 N-(4-Fluorophenyl)-[1-(2-pyridylmethyl)
indol-3-yl]glyoxylamide

EXAMPLE 12

D 24850 N-(4-Fluorophenyl)-[1(3-pyridylmethyl)
indol-3-yl]glyoxylamide

EXAMPLE 13

D 24851 N-(Pyridin-4-yl)-[1-(4-chlorobenzyl)indol-3-yl]glyoxylamide

EXAMPLE 14

D 24852 N-(Pyridin-4-yl)-[1-(2-chlorobenzyl)indol-3-yl]glyoxylamide

EXAMPLE 15

D 24853 N-(Pyridin-2-yl)-[1-(4-fluorobenzyl)indol-3-yl]glyoxylamide

EXAMPLE 16

D 24847 N-(Pyridin-4-yl)-[1-(2-pyridylmethyl)
indol-3-yl]glyoxylamide

EXAMPLE 17

D 24858 (4-Phenylpiperazin-1-yl)-[1-(4-fluorobenzyl)indol-3-yl]glyoxylamide

EXAMPLE 18

D 24854 N-(Pyridin-2-yl)-(1-benzylindol-3-yl)
glyoxylamide

EXAMPLE 19

D 25421 N-(Pyridin-4-yl)-[1-(4-fluorobenzyl)-6-ethoxycarbonylamino-indol-3-yl]glyoxylamide

EXAMPLE 20

D 25422 N-(Pyridin-4-yl)-[1-(4-fluorobenzyl)-5-ethoxycarbonylamino-indol-3-yl]glyoxylamide

EXAMPLE 21

D 25423 N-(Pyridin-4-yl)-[1-(4-fluorobenzyl)-6-cyclopentyloxycarbonyl-aminoindol-3-yl]
glyoxylamide

EXAMPLE 22

D 25420 4-(Pyridin-4-yl)piperazin-1-yl)-[1-(4-fluorobenzyl)indol-3-yl]-glyoxylamide

EXAMPLE 23

D 24866 N-(3,4,5-Trimethoxybenzyl)-N-(allylaminocarbonyl-2-methylprop-1-yl)-[1-(4-fluorobenzyl)indol-3-yl]glyoxylamide

EXAMPLE 24

N-(Pyridin-4-yl)-[1-(4-fluorobenzyl)-5-methoxyindol-3-yl]-glyoxylamide

EXAMPLE 25

N-(Pyridin-4-yl)-[1-(4-fluorobenzyl)-5-ethoxycarbonylamino-methylindol-3-yl]
glyoxylamide Starting substances for the compounds of the general formula 1 prepared according to synthesis scheme 1, which are evident from Table 1.

For the synthesis final products

| D 24241 | D 24242 | D 24834 | D 24835 |
| D 24836 | D 24840 | D 24841 | D 24842 |
| D 24843 | D 24848 | D 24849 | D 24850 |
| D 24851 | D 24852 | D 24853 | D 24847 |
| D 24858 | D 24854 | D 25420 | D 25422 |
| D 25421 | D 25423 | | | all precursors are commercially available.

Furthermore, the compounds of the general formula 1 with Z=O, $R_1$=aryl, aralkyl, heteroaryl, heteroaralkyl and the allylamino-carbonyl-2-methylprop-1-yl group and $R_2$=alkyl, aralkyl and the heteroaralkyl group are also obtainable according to the synthesis route of Scheme 2:

Scheme 2

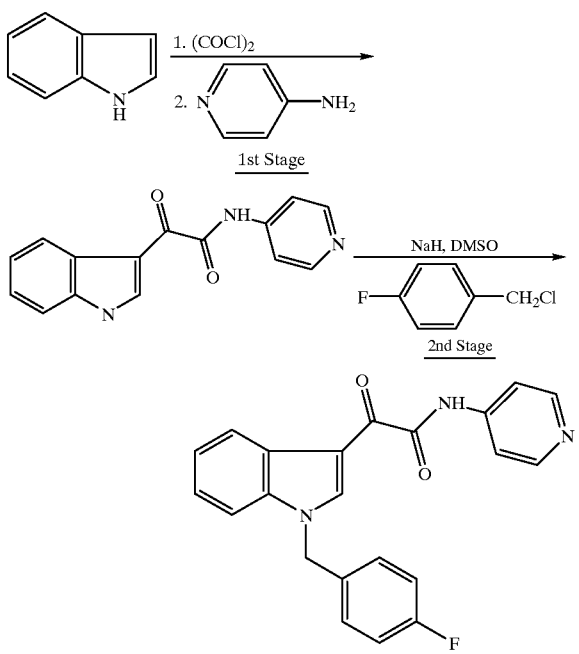

The compounds D 24241, D 24841, D 24840 and D 24834 (2nd Stage of reaction scheme 2, see also Table 1) and their respective precursors D 24825, D 24831, D 24832 and D 24833 (1st Stage of reaction scheme 2, see also Table 2 on page K) were obtained according to the present Scheme 2.

N-(Pyridin-4-yl)-[1-(4-fluorobenzyl)indol-3-yl]-glyoxylamide (D 24241)

1st Stage

N-(Pyridin-4-yl)-(indol-3-yl)glyoxylamide

A solution of 10 g (85.3 mmol) of indole in 100 ml of ether is added dropwise at 0° C. to a solution of 9 ml of oxalyl chloride in 100 ml of anhydrous ether. The mixture is kept under reflux for 3 hours. A suspension of 12 g (127.9 mmol) of 4-aminopyridine in 500 ml of tetrahydrofuran is then added dropwise at −5° C., the reaction mixture is heated to reflux temperature with stirring for 3 hours and allowed to stand overnight at room temp. It is filtered, the precipitate is treated with water and the dried compound is purified on a silica gel column (silica gel 60, Merck AG, Darmstadt) using the eluent methylene chloride/ethanol (10:1, v/v).

Yield: 9.8 g (43.3% of theory)

M.p.: from 250° C.

2nd Stage

N-(Pyridin-4-yl)-[1(4-fluorobenzyl)indol-3-yl]-glyoxylamide (D 24241)

The N-(pyridin-4-yl)-(indol-3-yl)glyoxylamide obtained according to the 1st Stage is reacted with 4-fluorobenzyl chloride according to the "benzylation procedure" (page 5) and the compound D 24241 obtained is isolated.

Yield: 41% of theory
M.p.: 224–225° C.
Elemental analysis

| | | | |
|---|---|---|---|
| calc. | C 70.77 | H 4.32 | N 11.25 |
| found | C 70.98 | H 4.40 | N 11.49 |

General procedure for the preparation of the compounds of the general formula 1 according to Scheme 2

1st Stage

The indol derivative, which can be unsubstituted or substituted on C-2 or in the phenyl ring, dissolved in a solvent, as, for example, indicated above for oxalyl chloride, is added dropwise at a temperature between −5° C. and +5° C. to a solution prepared under a nitrogen atmosphere of a monomolar up to 60% excess amount of oxalyl chloride in an aprotic or nonpolar solvent, such as, for example, in diethyl ether, methyl tert-butyl ether, tetrahydrofuran, dioxane or alternatively dichloromethane. The reaction solution is then heated for 1 to 5 hours to a temperature between 10° C. and 120° C., preferably between 20° C. and 80° C., particularly between 30° C. and 60° C., and the solvent is then evaporated. The residue of the (indol-3-yl)glyoxyloyl chloride which remains is dissolved or suspended in an aprotic solvent, such as, for example, tetrahydrofuran, dioxane, diethyl ether, toluene or alternatively in a dipolar aprotic solvent, such as, for example, dimethylformamide, dimethylacetamide or dimethyl sulfoxide, cooled to a temperature between −10° C. and +10° C., preferably to −5° C. to 0° C., and treated in the presence of an acid scavenger with a solution of the primary or secondary amine in a diluent. Possible diluents are the solvents used for dissolving the "indolyl-3-glyoxyloyl chloride". Acid scavengers used are triethylamine, pyridine, dimethylaminopyridine, basic ion exchanger, sodium carbonate, potassium carbonate, powdered potassium hydroxide and excess primary or secondary amine employed for the reaction.

The reaction takes place at a temperature from 0° C. to 120° C., preferably at 20–80° C., particularly between 40° C and 60° C. After a reaction time of 1–4 hours and standing at room temperature for 24 hours, the mixture is filtered, the precipitate is digested with water, filtered off with suction and dried in vacuo. The desired compound is purified by recrystallization in an organic solvent or by column chromatography on silica gel or alumina. The eluent used is, for example, a mixture of dichloromethane and ethanol (10:1, vol/vol).

2nd Stage

The "indol-3-ylglyoxylamide" obtained according to the above procedure of the 1st Stage is dissolved in a protic, dipoplar aprotic or nonpolar organic solvent, such as, for example, in isopropanol, tetrahydrofuran, dimethyl sulfoxide, dimethylformamide, dimethylacetamide, N-methylpyrrolidone, dioxane, toluene or methylene chloride and added dropwise to a suspension of a base prepared in a three-necked flask under an $N_2$ atmosphere or employed in a molar amount or in excess, such as, for example, sodium hydride, powdered potassium hydroxide, potassium tert-butoxide, dimethylaminopyridine or sodium amide in a suitable solvent. The desired alkyl, aralkyl or heteroaralkyl halide is then added either undiluted or in a diluent, which was also used, for example, for dissolving the "indol-3-ylglyoxylamide", if appropriate with addition of a catalyst, such as, for example, copper and the mixture is allowed to react for some time, e.g. for 30 minutes to 12 hours, and the temperature is kept within a range between 0° C. and 120° C., preferably between 30° C. and 80° C., particularly between 50 and 70° C. After completion of the reaction, the reaction mixture is added to water, the solution is extracted, for example, with diethyl ether, dichloromethane, chloroform, methyl tert-butyl ether, tetrahydrofuran or n-butanol and the organic phase obtained in each case is dried using anhydrous sodium sulfate.

The organic phase is concentrated in vacuo, the residue which remains is crystallized by trituration or the oily residue is purified by distillation or by column or flash chromatography on silica gel or alumina. The eluent used is, for example, a mixture of methylene chloride and diethyl ether in the ratio 8:2 (vol/vol) or a mixture of methylene chloride and ethanol in the ratio 9:1 (v/v)

According to this general procedure for stages 1 and 2, on which the synthesis scheme 2 is based, the compounds D 24241, D 24841, D 24840 and D 24834 were synthesized, which have also already been prepared according to the synthesis procedure of reaction scheme 1 and are evident from Table 1. The relevant precursors of these compounds can be seen from Table 2 on page K and L.

The compounds show a good dose-dependent antitumor action in the following pharmacological models:

The indoles, particularly D-24851 and D-24241, are first apparent in the XTT proliferation test/cytotoxicity test (Table 3 and Table 3a). In this test system, the effect of substances on the proliferation behavior of tumor cell lines is investigated. In the course of this, the cytotoxic potential of these substances is determined. The test method is described in Scudiero et al. 1988, *Cancer Res.* 48, 4827.

The following tumor cell lines were employed in the investigations:

The KB cell line an epidermal carcinoma of the oral cavity, the L1210 cell line a lymphatic leukemia of the mouse, the LNCAP cell line a prostate carcinoma and the SK-OV-3 cell line an ovarian carcinoma.

A large number of different indols were active in all four tumor cell lines. D-24851 and D-24241 showed the strongest actions, D-24851 being more active than D-24241 (Table 3 and 4).

In further comparative investigations with D-24851 and D-24241 in the hollow fiber assay on the nude mouse and on L 1210 (mouse), a strong dose-dependent antitumor action was observed for both compounds (Table 3 and 5). In the hollow fiber assay, both compounds were almost equally strongly active, while on L 1210 D-24851 was markedly more strongly active after oral and intraperitoneal administration than D-24241. In comparison with the antitumor substances available on the market, D-24851 is markedly more strongly active in many cases in the leukemia model than the known comparison substances (Table 5).

A further great advantage of D-24851 in comparison with the antitumor substances available on the market is the low toxicity of the compound (Tables 3 and 5). With LD 50 values of 1000 mg/kg p.o. and >1000 mg/kg i.p., the compound has a great therapeutic breadth.

Furthermore, after administration of D-24851 no DNA fragmentation was observed. In the hematopoiesis test, too, none of the blood parameters investigated were modified by the intraperitoneal administration of D-24851.

In a further chemotherapy model, the Dunning tumor in the rat, a stoppage of tumor growth and in some animals even tumor regression was observed after repeated oral administration of D24851.

In the KB test on the nude mouse, an antitumor action was likewise observed after administration of the two indols D-24851 and D-24241 (Tables 3, 3a and 4).

In the investigations with the tumor cell line L1210, a lymphatic leukemia of the mouse, a distinct dose-dependent prolongation of the survival time was seen after intraperitoneal or oral administration of D 24851 with a 100 and 147 mg/kg multiple dose (FIG. 1*a* and FIG. 1*b*).

On account of the good therapeutic breadth, which was demonstrated experimentally, the active substance can be administered in a higher amount than commercially available tumor pharmaceuticals.

Without wishing to restrict the scope of the invention by the following details, it can be said that doses from approximately 20 mg up to 500 mg daily are possible orally. In the case of intravenous administration as an injection or as an infusion, up to 250 mg/day or more can be administered depending on the body weight of the patient and individual tolerability.

TABLE 1a

Indolylglyoxylamides according to reaction scheme 1

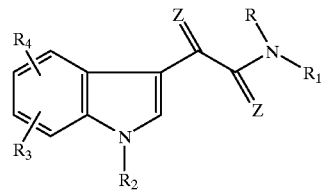

Formula I

| Example | D | R | $R_1$ | $R_2$ | $R_3$ | $R_4$ | Z | M.p. |
|---|---|---|---|---|---|---|---|---|
| 1 | D-24241 | H | pyridyl | —CH$_2$—C$_6$H$_4$—F | H | H | O | 225–6° C. |
| 2 | D-24242 | H | pyridyl | CH$_3$ | H | H | O | 176° C. |

TABLE 1a-continued

Indolylglyoxylamides according to reaction scheme 1

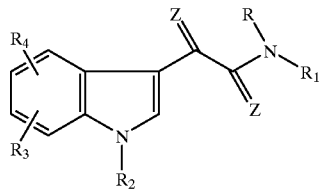

Formula I

| Example | D | R | $R_1$ | $R_2$ | $R_3$ | $R_4$ | Z | M.p. |
|---|---|---|---|---|---|---|---|---|
| 3 | D-24834 | H | 3-pyridyl | $-CH_2-$(4-F-phenyl) | H | H | O | 173° C. |
| 4 | D-24835 | H | 3-pyridyl | $-CH_2-$phenyl | H | H | O | 140° C. |
| 5 | D-24836 | H | 3-pyridyl | $-CH_2-$(2-Cl-phenyl) | H | H | O | 185° C. |

TABLE 1b

Indolylglyoxylamides according to reaction scheme 1

| Example | | R | $R_1$ | $R_2$ | $R_3$ | $R_4$ | Z | M.p. |
|---|---|---|---|---|---|---|---|---|
| 6 | D-24840 | H | 4-F-phenyl | $-CH_2-$(4-F-phenyl) | H | H | O | 199° C. |
| 7 | D-24841 | H | 4-$NO_2$-phenyl | $-CH_2-$(4-F-phenyl) | H | H | O | >250° C. |
| 8 | D-24842 | H | 2-Cl-3-pyridyl | $-CH_2-$(4-F-phenyl) | H | H | O | 149° C. |
| 9 | D-24843 | H | 4-pyridyl | $-CH_2-$phenyl | H | H | O | 178–180° C. |
| 10 | D-24848 | H | 4-pyridyl | $-CH_2-$(3-pyridyl) | H | H | O | 179° C. |
| 11 | D-24849 | H | 4-F-phenyl | $-CH_2-$(2-pyridyl) | H | H | O | 132° C. |

TABLE 1c

Indolylglyoxylamides according to reaction scheme 1

| Example D | R | R₁ | R₂ | R₃ | R₄ | Z | M.p. |
|---|---|---|---|---|---|---|---|
| 12 D-24850 | H | 4-F-phenyl | —CH₂-(pyridin-3-yl) | H | H | O | 144° C. |
| 12 D-24851 | H | pyridin-4-yl | —CH₂-(4-Cl-phenyl) | H | H | O | 262° C. |
| 14 D-24852 | H | pyridin-4-yl | —CH₂-(2-Cl-phenyl) | H | H | O | 184° C. |
| 15 D-24853 | H | pyridin-2-yl | —CH₂-(4-F-phenyl) | H | H | O | 141° C. |
| 16 D-24847 | H | pyridin-4-yl | —CH₂-(pyridin-2-yl) | H | H | O | 202° C. |
| 17 D-24858 | R + R₁ together | 4-(piperidin-1-yl)phenyl | —CH₂-(4-F-phenyl) | H | H | O | 115° C. |
| 18 D-24854 | H | pyridin-2-yl | —CH₂-phenyl | H | H | O | 112–3° C. |

TABLE 1d

Indolylglyoxylamides according to reaction scheme 1

| Example D | R | R₁ | R₂ |
|---|---|---|---|
| 19 D 25421 | H | pyridin-4-yl | —CH₂-(4-F-phenyl) |
| 20 D 25422 | H | pyridin-4-yl | —CH₂-(4-F-phenyl) |
| 21 D 25423 | H | pyridin-4-yl | —CH₂-(4-F-phenyl) |
| 22 D 25420 | R + R₁ together | 4-(piperidin-1-yl)phenyl | —CH₂-(4-F-phenyl) |

TABLE 1d-continued

Indolylglyoxylamides according to reaction scheme 1

| 23 D-24866 | -CH₂-(2,3,4-trimethoxyphenyl) | (CH₃)₂CH-CH₂-CH(C(=O)NH-allyl)- | -CH₂-(4-F-phenyl) |
| 24 D-25561 | H | 4-pyridylmethyl | -CH₂-(4-F-phenyl) |
| 25 D-25559 | H | 4-pyridylmethyl | -CH₂-(4-F-phenyl) |

| Example D | R₃ | R₄ | Z | M.p. |
|---|---|---|---|---|
| 19 D 25421 | 6-NHCOOEt | H | O | >250° C. |
| 20 D 25422 | 5-NHCOOEt | H | O | 183° C. |
| 21 D 25423 | 6-NHCOO-cyclopentyl | H | O | |
| 22 D 25420 | H | H | O | 160–62° C. |
| 23 D-24866 | H | H | O | 139–141° C. |
| 24 D-25561 | 5-OCH₃ | H | O | 188° C. |
| 25 D-25559 | 5-CH₂—NHCOOEt | H | O | 175–176° C. |

TABLE 1e

Indole-3-glyoxylic acid derivative according to reaction scheme 1

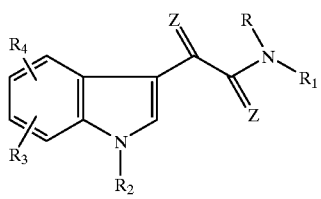

Formula 1

| Example, D- | R | R₁ | R₂ | R₃ | R₄ | Z | M.p |
|---|---|---|---|---|---|---|---|
| 26 D-50570 | H | 4-pyridylmethyl | -CH₂-(3,4-dichlorophenyl) | H | H | O | |

TABLE 1e-continued
Indole-3-glyoxylic acid derivative according to reaction scheme 1
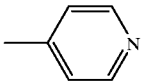
Formula 1
| Example, D- | R | R₁ | R₂ | R₃ | R₄ | Z | M.p |
|---|---|---|---|---|---|---|---|
| 27 D-51076 | H | 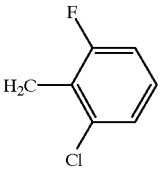 | 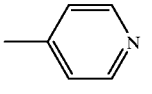 | H | H | O | |
| 28 D-49404 | H | 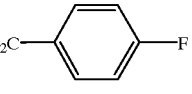 | 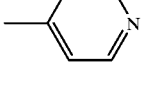 | 5-F | H | O | 205–207° C. |
| 29 D-44073 | H | 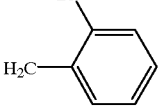 | 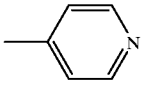 | H | H | O | 192–194° C. |
| 30 D-44072 | H | 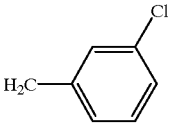 | 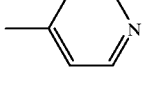 | H | H | O | 196–198° C. |
| 31 D-44067 | H | 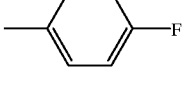 | 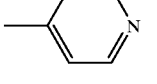 | H | H | O | 219–221° C. |
TABLE 1f
Indole-3-glyoxylic acid derivatives according to reaction scheme 1
| Example, D- | R | R₁ | R₂ | R₃ | R₄ | Z | M.p. |
|---|---|---|---|---|---|---|---|
| 32 D-44061 | H | 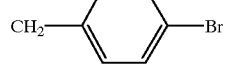 | 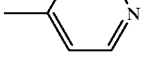 | H | H | O | 238–240° C. |
| 33 D-43163 | H | 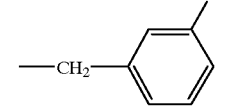 | 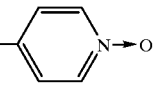 | H | H | O | 203–205° C. |
| 34 D-51273 | H | 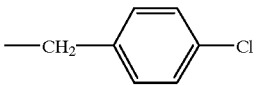 |  | H | H | O | 305–307° C. |

TABLE 1f-continued

Indole-3-glyoxylic acid derivatives according to reaction scheme 1

| Example, D- | R | R₁ | R₂ | R₃ | R₄ | Z | M.p. |
|---|---|---|---|---|---|---|---|
| 35 D-44070 | H | 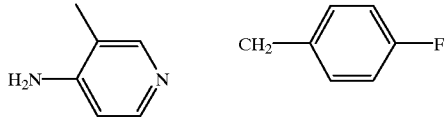 |  CH₂—C₆H₄—F | H | H | O | >250° C. |
| 36 D-49405 | H | 4-CN-C₆H₄— | CH₂—C₆H₄—F | H | H | O | 237–239° C. |
| 37 D-44071 | H | 3-COOEt-C₆H₄— | CH₂—C₆H₄—F | H | H | O | 154–156° C. |
| 38 D-44069 | H | 2-Cl-4-NO₂-C₆H₃— | CH₂—C₆H₄—F | H | H | O | 213–215° C. |
| 39 D-44068 | H | 2-NO₂-4-Cl-C₆H₃— | CH₂—C₆H₄—F | H | H | O | 183–185° C. |

TABLE 1g

Indole-3-glyoxylic acid derivatives according to reaction scheme 1

| Example, D- | R | R₁ | R₂ | R₃ | R₄ | Z | M.p. |
|---|---|---|---|---|---|---|---|
| 40 D-44066 | H | 4-Br-C₆H₄— | CH₂—C₆H₄—F | H | H | O | 187–189° C. |
| 41 D-49406 | H | 4-pyridyl— | CH₂—C₆H₄—F | 5-CH₂—NH—COOCH₃ | H | O | 191–193° C. |
| 42 D-49403 | H | 4-pyridyl— | CH₂—C₆H₄—F | 5-CH₂—NH—CO—O—CH₂—CH(CH₃)₂ | H | O | 193–195° C. |
| 43 D-44064 | H | 3,4,5-(OCH₃)₃-C₆H₂— | CH₂—C₆H₄—F | H | H | O | 104–106° C. |

TABLE 1g-continued

Indole-3-glyoxylic acid derivatives according to reaction scheme 1

| Example, D- | R | R$_1$ | R$_2$ | R$_3$ | R$_4$ | Z | M.p. |
|---|---|---|---|---|---|---|---|
| 44 D-43156 | H | 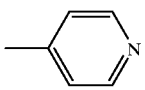 | 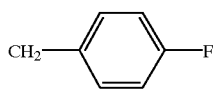 | 6-NO$_2$ | H | O | 238–240° C. |
| 45 D-43155 | H | 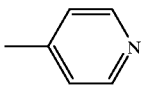 | 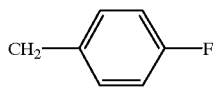 | 5-NO$_2$ | H | O | 203–205° C. |
| 46 D-43152 | H | 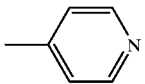 | 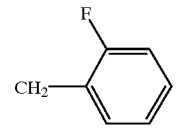 | H | H | O | 196–198° C. |
| 47 D-43151 | H | 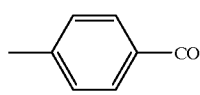 | 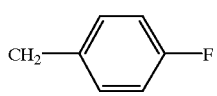 | H | H | O | 141–143° C. |

TABLE 1h

Indole-3-glyoxylic acid derivatives according to reaction scheme 1

| Example, D- | R | R$_1$ | R$_2$ | R$_3$ | R$_4$ | Z | M.p. |
|---|---|---|---|---|---|---|---|
| 48 D-43149 | H | 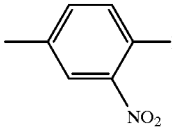 | 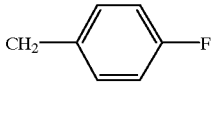 | H | H | O | 202–204° C. |
| 49 D-43148 | H | 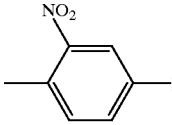 | 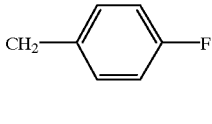 | H | H | O | 183–185° C. |
| 50 D-25505 hydrochloride | H | 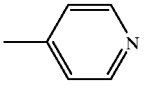 | 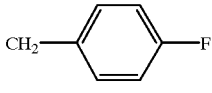 | H | H | O | hydrochloride |
| 51 D-51133 trifluoroacetate | H | 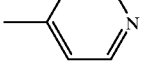 | 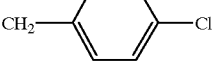 | H | H | O | 251–253° C. trifluoroacetate |
| 52 D-51128 | H | 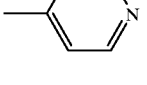 | 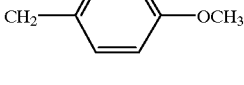 | H | H | O | 173–174° C. |
| 53 D-51077 | H | 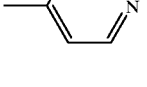 | 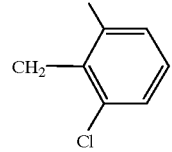 | H | H | O | 244–245° C. |

TABLE 1h-continued
Indole-3-glyoxylic acid derivatives according to reaction scheme 1
| Example, D- | R | R₁ | R₂ | R₃ | R₄ | Z | M.p. |
|---|---|---|---|---|---|---|---|
| 54 D-51195 | H | 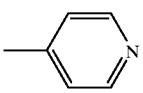 | 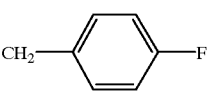 | 5-NH—CO—O—CH₂—CH(CH₃)₂ 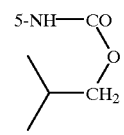 | H | O | 228–230° C. |
| 55 D-51391 | H | 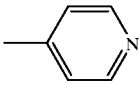 | 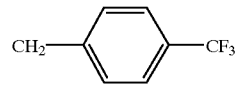 | H | H | O | 270–271° C. |
TABLE 1i
Indole-3-glyoxylic acid derivatives according to reaction scheme 1
| Example, D- | R | R₁ | R₂ | R₃ | R₄ | Z | M.p. |
|---|---|---|---|---|---|---|---|
| 56 D-51393 | H | 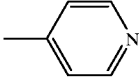 | 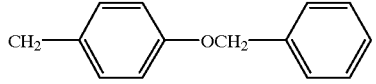 | H | H | O | Öl |
| 57 D-51394 | H | 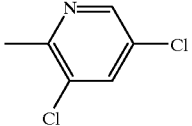 | 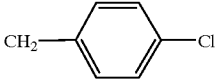 | H | H | O | 216–218° C. |
| 58 D-51184 | H | 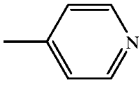 | 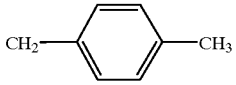 | H | H | O | 215–217° C. |
| 59 D-51185 | H | 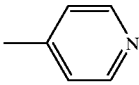 | 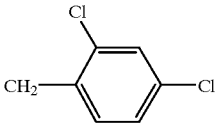 | H | H | O | 241–242° C. |
| 60 D-25463 | H | 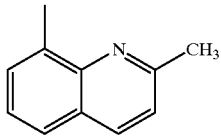 | 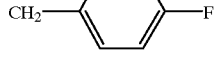 | H | H | O | ° C. |
| 61 D-24584 | H | 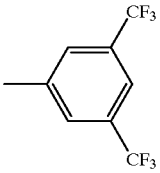 | 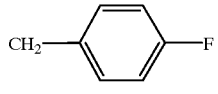 | H | H | O | ° C. |
| 62 D-25320 | H | 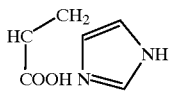 | 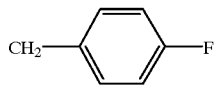 | H | H | O | 145–147° C. |

TABLE 1j

Indole-3-glyoxylic acid derivatives according to reaction scheme 1

| Example, D- | R | $R_1$ | $R_2$ | $R_3$ | $R_4$ | Z | M.p. |
|---|---|---|---|---|---|---|---|
| 63 D-51396 | R,R together: 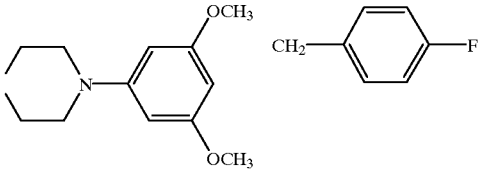 | | $CH_2$-C6H4-F (4-F) | H | H | O | 137° C. |
| 64 D-44065 | R,$R_1$ together: 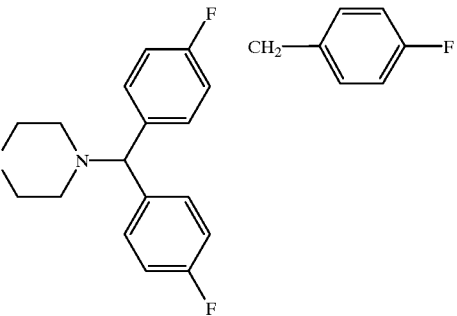 | | $CH_2$-C6H4-F | H | H | O | 205–207° C. |
| 65 D-43146 | R,$R_1$ together:  | | $CH_2$-C6H4-F | H | H | O | 89–91° C. |
| 66 D-43145 | R,$R_1$ together: 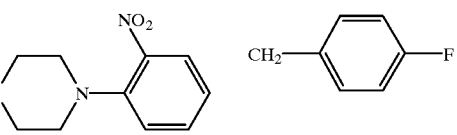 | | $CH_2$-C6H4-F | H | H | O | 68–70° C. |
| 67 D-25558 | R,$R_1$ together: 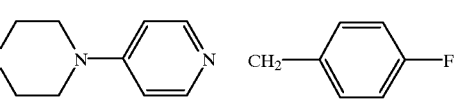 | | $CH_2$-C6H4-F | 6-NHCOOC$_2$H$_5$ | H | O | oil |

TABLE 2

Indolylglyoxylamides according to reaction scheme 2

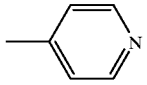

Formula 1

| Example, D- | R | $R_1$ | $R_2$ | $R_3$ | $R_4$ | Z | M.p. |
|---|---|---|---|---|---|---|---|
| 1 D-24825 | H | 4-methylpyridyl | H | H | H | O | >250° C. |
| 2 D-24831 | H | 4-NO$_2$-phenyl | H | H | H | O | >250° C. |

TABLE 2-continued

Indolylglyoxylamides according to reaction scheme 2

Formula 1

| Example, D- | R | R$_1$ | R$_2$ | R$_3$ | R$_4$ | Z | M.p. |
|---|---|---|---|---|---|---|---|
| 3 D-24832 | H | 4-F-phenyl | H | H | H | O | 233–5° C. |
| 4 D-24833 | H | 3-pyridyl | H | H | H | O | 235° C. |

TABLE 2b

Indol-3-glyoxylic acid derivatives according to reaction scheme 1

| Example, D- | R | R$_1$ | R$_2$ | R$_3$ | R$_4$ | Z | M.p. |
|---|---|---|---|---|---|---|---|
| 5 D-43154 | H | 4-pyridyl | H | 6-NO$_2$ | H | O | 250° C. (dec.) |
| 6 D-43153 | H | 4-pyridyl | H | 5-NO$_2$ | H | O | >250° C. |
| 7 D-25319 | H | -HC(COOH)-CH$_2$-imidazole | H | H | H | O | 156–157° C. |

TABLE 2a

Indolylglyoxylamides according to reaction scheme 2

| Example, D- | R | R$_1$ | R$_2$ | R$_3$ | R$_4$ | Z | M.p. |
|---|---|---|---|---|---|---|---|
| 5 D-43154 | H | 4-pyridyl | H | 6-NO$_2$ | H | O | 250° C. (dec.) |
| 6 D-43153 | H | 4-pyridyl | H | 5-NO$_2$ | H | O | >250° C. |
| 7 D-25319 | H | -HC(COOH)-CH$_2$-imidazole | H | H | H | O | 156–157° C. |

TABLE 3

Composition D-24851 according to Example 13
D-24851 N-(Pyridin-4-yl)-[1-(4-chlorobenzyl)indol-3-yl]glyoxylamide

| Model | Result. | SK-OV-3 | KB | L1210 | LNCaP | MCF-7 | Tox |
|---|---|---|---|---|---|---|---|
| XTT (μg/ml) | EC$_{50}$ | ≈0.03 | ≈0.017 | ≈0.017 | ≈0.03 | | |
| 1 × ip (mg/kg) | LD$_{50}$ | | | | | | =1000 |
| 1 × per os (mg/kg) | LD$_{50}$ | | | | | | >1000 |
| Hollow fiber intraperitoneal 4 × 46 mg/kg ip | % INH | | no action | 56 | | 38 | |
| Hollow fiber intraperitoneal 4 × 147 mg/kg ip | % INH | | 12 | 60 | | 68 | |
| Hollow fiber subcutaneous 4 × 46 mg/kg ip | % INH | | 44 | no action | | 47 | |
| Hollow fiber subcutaneous 4 × 147 mg/kg ip | % INH | | 35 | 67 | | 68 | |
| In vivo: | | | | | | | |
| 1 × 681 mg/kg ip | % ILS | | | 0 | | | |
| 1 × 464 mg/kg ip | | | | 18 | | | |
| 4 × 215 mg/kg ip | % ILS | | | 13 | | | |
| 4 × 147 mg/kg ip | | | | 94 | | | |

TABLE 3-continued

Composition D-24851 according to Example 13
D-24851 N-(Pyridin-4-yl)-[1-(4-chlorobenzyl)indol-3-yl]glyoxylamide

| Model | Result. | SK-OV-3 | KB | L1210 | LNCaP | MCF-7 | Tox |
|---|---|---|---|---|---|---|---|
| 7 × 100 mg/kg ip | % ILS | | | 35 | | | |
| 7 × 147 mg/kg ip | | | | 59 | | | |
| 1 × 681 mg/kg po | % ILS | | | 22 | | | |
| 4 × 215 mg/kg po | | | | 31 | | | |
| 7 × 100 mg/kg po | | | | 63 | | | |
| 7 × 147 mg/kg po | | | | 75 | | | |
| 7 × 46 mg/kg ip | % WHI | | 33 | | | | |
| 2 × 215 mg/kg po | | | 18 | | | | |

TABLE 3 a

| Substance according to Example (D Number) | Tumor cells XTT | | | |
|---|---|---|---|---|
| | KB EC$_{50}$ [μg/ml] | L 1210 EC$_{50}$ [μg/ml] | LNCAP EC$_{50}$ [μg/ml] | SK-OV-3 EC$_{50}$ [μg/ml] |
| 1 (D 24241) | 0.020 | 0.170 | >31.600 | 0.170 |
| 3 (D 24834) | 1.75 | 1.75 | 9.250 | 1.750 |
| 4 (D 24835) | 17.5 | 1.750 | >31.6 | 9.200 |
| 6 (D 24840) | 3.100 | 1.750 | >31.6 | 17.5 |
| 9 (D 24843) | 0.050 | 0.090 | 3.240 | 1.750 |
| 10 (D 24848) | 4.060 | 1.75 | >31.6 | 7.220 |
| 11 (D 24849) | 4.590 | 1.750 | 17.500 | 4.250 |
| 12 (D 24850) | >31.6 | 0.017 | >31.6 | >31.6 |
| 13 (D 24851) | 0.017 | 0.017 | 0.030 | 0.030 |
| 14 (D 24852) | 1.75 | 1.75 | 17.5 | 2.58 |
| 15 (D 24853) | >31.6 | 3.1 | >31.6 | >31.6 |
| 16 (D 24847) | 4.59 | 1.75 | 17.500 | 4.250 |
| Table 2 (D 24831) | 17.5 | 17.5 | 17.5 | 17.5 |

Further animal experimental results:

Stoppage of tumor growth, in some animals even tumor regression, was observed in the Dunning tumor after administration of 7×100 mg/kg and 7×147 mg/kg p.o. of D-24851.

In comparison with the original form, the testing of the crystalline form yielded no differences.

D-24851 causes no DNA fragmentation

In the hematopoiesis test, none of the blood parameters investigated were altered by the intraperitoneal administration of D-24851.

TABLE 4

D 24241 N-(Pyridin-4-yl)-[1-(4-fluorobenzyl)indol-3-yl]glyoxylamide according to Example 1

| Model | Result. | SK-OV-3 | KB | L1210 | LNCaP | MCF-7 | Tox |
|---|---|---|---|---|---|---|---|
| XTT (μg/ml) | EC$_{50}$ | ≈0.17 | ≈0.02 | ≈0.17 | >31.6 | | |
| 1 × ip (mg/kg) | LD$_{50}$ | | | | | | ≈158 |
| 1 × per os (mg/kg) | LD$_{50}$ | | | | | | >1000 |
| Hollow fiber intraperitoneal 4 × 15.8 mg/kg ip | % INH | | 46 | 43 | | no action | |
| Hollow fiber subcutaneous 4 × 15.8 mg/kg ip | % INH | | 81 | 68 | | 33 | |
| In vivo: | | | | | | | |
| 1 × 14.7 mg/kg ip | % ILS | | | | no action | | |
| 1 × 30 mg/kg per os | % ILS | | | | no action | | |
| 1 × 464 mg/kg per os | % ILS | | | | 44 | | |
| 4 × 30 mg/kg per os | % ILS | | | | no action | | |
| 6 × 30 mg/kg per os | % ILS | | | | no action | | |
| 14 × 30 mg/kg per os | % ILS | | | | no action | | |
| 19 × 50 mg/kg per os | % ILS | | | | 50 | | |
| 2 × 46.4 mg/kg ip | % WHI | | | 22 | | | |
| 4 × 21.5 mg/kg ip | % WHI | | | no action | | | |
| 2 × 215 mg/kg po | % WHI | | | 47 | | | |

TABLE 5

Comparison of the antitumor action of D-24851 and D-24241 with standard compounds

| Substance | Tox. mg/kg | L1210 mg/kg | XTT EC 50 (µg/ml) |
|---|---|---|---|
| D-24851 | ≈1000 i.p. | 4 × 147 i.p. 94% ILS | KB ≈ 0.017 L1210 ≈ 0.017 SKOV3 ≈ 0.03 LNCAP ≈ 0.03 |
| D-24241 | ≈158 i.p. | 19 × 50 p.o. 50% ILS | KB ≈ 0.02 L1210 ≈ 0.07 SKOV3 ≈ 0.17 LNCAP > 31.6 |
| Mitoxantrone | 16 i.v. | 1 × 4.64 i.v. 144% ILS | KB ~ 0.174 L1210 < 0.0003 SKOV3 ~ 0.174 LNCAP ~ 0.017 |
| 5-Fluorouracil | — | 1 × 147 i.p. 72% ILS 4 × 68.1 i.p. 83% ILS | — |
| Methotrexate | — | 1 × 53.7 i.p. 39% ILS | KB ~ 0.007 L1210 n.d. SKOV3 > 31.6 LNCAP n.d. |
| Etoposide | ≈ 158.0 i.p. >68.1 i.v. | 1 × 46.4 i.p. 56% ILS | — |
| Ratjadone | ~ 16.0 i.p. ~ 30.0 i.v. | 1 × 1.47 i.p. 22% ILS | KB < 0.003 L1210 < 0.003 SKOV3 < 0.003 LNCAP < 0.003 |
| Epothilone B | ≈ 100.0 i.p. | 1 × 10 i.p. 44% ILS | KB ~ 0.0002 L1210 ~ 0.0017 SKOV3 ~ 0.0031 LNCAP ~ 0.014 |
| Taxol | ≈ 158 i.p. | 1 × 14.7 i.v. 22% ILS 1 × 46.4 i.v. 61% ILS | KB < 0.003 L1210 < 0.003 SKOV3 < 0.003 LNCAP < 0.003 |
| Vincristine | ≈ 3.0 i.v. | 1 × 1.0 i.p. 29% ILS | KB < 0.001 L1210 0.004 SKOV3 0.003 LNCAP 0.004 |
| Adriamycin | ≈ 27.0 i.v. | 1 × 14.7 i.v. 111% ILS | KB 0.15 L1210 0.174 SKOV3 0.089 LNCAP 0.17 |
| Cisplatin | ≈ 16.0 i.p. ≈ 73.0 p.o. | 1 × 3.16 i.p. 38.9% ILS | L1210 0.30 |
| Carboplatin | ≈ 158.0 i.p. ≈ 841.0 p.o | 1 × 100 i.p. 41% ILS | — |
| Lobaplatin | ≈ 34.0 i.p. | 1 × 14.7 i.p. 55.0% ILS | — |
| Cyclophosphamide | ≈ 340.7 i.v. | 1 × 46.4 i.v. 40% ILS | — |
| Ifosfamide | ≈ 732 i.p. | 1 × 316 i.p. 89% ILS | — |
| Miltefosine | ≈ 46.4 i.p. ≈ 464–1000 p.o. | no action | — |

What is claimed is:

1. A method of using an N-substituted indole-3-glyoxylamide of formula 1 as an antitumor agent,

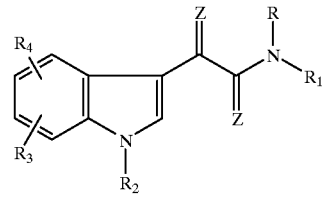

Formula 1 where the radicals R, $R_1$, $R_2$, $R_3$, $R_4$ and Z have the following meanings:

R=hydrogen, $(C_1-C_6)$-alkyl, where the alkyl group is optionally mono- or polysubstituted by a phenyl ring and this phenyl ring for its part is optionally mono- or polysubstituted by halogen, $(C_1-C_6)$-alkyl, $(C_3-C_7)$-cycloalkyl, by carboxyl groups, carboxyl groups esterified with $C_1-C_6$-alkanols, trifluoromethyl groups, hydroxyl groups, methoxy groups, ethoxy groups, benzyloxy groups or by a benzyl group which is mono- or polysubstituted in the phenyl moiety by $(C_1-C_6)$-alkyl groups, halogen atoms or trifluoromethyl groups, or R is a benzyloxycarbonyl group or a tertiary-butoxycarbonyl radical (BOC radical), or an acetyl group, $R_1$ is a pyridine structure of formula 2

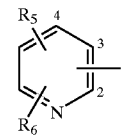

Formula 2 or its N-oxide, where the pyridine structure is alternatively bonded to the ring carbon atoms 2, 3 and 4 and is optionally substituted by the substituents $R_5$ and $R_6$; $R_5$ and $R_6$ are identical or different and signify $(C_1-C_6)$-alky, $(C_3-C_7)$-cycloalkyl, $(C_1-C_6)$-alkoxy, nitro, amino, hydroxyl, halogen, trifluoromethyl, ethoxycarbonylamino radical and a carboxyalkyloxy group in which the alkyl group has 1–4 C atoms;

$R_2$ is hydrogen or a $(C_1-C_6)$-alkyl group, where the alkyl group is mono- or polysubstituted by halogen and phenyl, which for its part is optionally mono or polysubstituted by halogen, $(C_1-C_6)$-alkyl, $(C_3-C_7)$-cycloalkyl, carboxyl groups, carboxyl groups esterified with $C_1-C_6$-alkanols, trifluoromethyl groups, hydroxyl groups, methoxy groups, ethoxy groups or benzyloxy groups, the $(C_1-C_6)$-alkyl group is optionally substituted by the 2-quinolyl group and the 2-, 3- and 4-pyridyl structure, which are optionally in each case mono- or polysubstituted by halogen, $(C_1-C_4)$-alkyl groups or $(C_1-C_4)$-alkoxy groups, or $R_2$ is an aroyl radical, where the aryl moiety on which the radical is based is a phenyl ring, which is optionally mono- or polysubstituted by halogen, $(C_1-C_6)$-alkyl, $(C_3-C_7)$-cycloalkyl, carboxyl groups, carboxyl groups esterified with $C_1-C_6$-alkanols, trifluoromethyl groups, hydroxyl groups, methoxy groups, ethoxy groups or benzyloxy groups;

$R_3$ and $R_4$ are identical or different and are hydrogen, $(C_1-C_6)$-alkyl, $(C_3-C_7)$-cycloalkyl, $(C_1-C_6)$-alkanoyl, $(C_1-C_6)$-alkoxy, halogen and benzyloxy, or a nitro group, an amino group, a $(C_1-C_4)$- mono or dialkyl-substituted amino group, or a ($C_1$–$C_6$) alkoxycarbonylamino function or ($C_1$–$C_6$)-alkoxycarbonylamino-($C_1$–$C_6$)-alkyl function; and Z is O or S;

said method comprising administering said N-substituted indole-3-glyoxylamide or an acid addition salt or N-oxide thereof to a subject in need of antitumor treatment.

2. The method according to claim 1 wherein said N-substituted indole-3-glyoxylamide is of the formula 1a

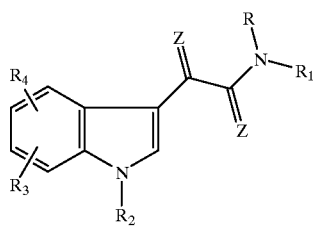

Formula 1a where the radicals
R=hydrogen
$R_1$=4 pyridyl,
$R_2$=benzyl, 4-chlorobenzyl, 4-fluorobenzyl, 3-pyridylmethyl, 4-bromobenzyl
$R_3$ and R=hydrogen and
Z is oxygen.

3. The method of claim 1 wherein an acid addition salt is administered which is the salt of a mineral acid, hydrochloric acid, sulfuric acid, phosphoric acid, or a salt of an organic acid, or N-oxide thereof.

4. The method of claim 3, wherein the organic acid is selected from the group consisting of acetic acid, lactic acid, malonic acid, maleic acid, lumaric acid, gluconic acid, glucuronic acid, citric acid, embonic acid, methanesulfonic acid, trifluoroacetic acid, succinic acid and 2-hydropoxyethanesulfonic acid.

5. Method of using N-substituted indole-3-glyoxylamides of the general formula 1

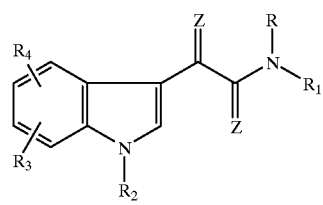

Formula 1 where the radicals R, $R_1$, $R_2$, $R_3$, $R_4$ and Z have the following meanings:

R=hydrogen, ($C_1$–$C_6$)-alkyl, where the alkyl group is optionally mono- or polysubstituted by a phenyl ring and this phenyl ring for its part is optionally mono- or polysubstituted by halogen, ($C_1$–$C_6$)-alkyl, ($C_3$–$C_7$)-cycloalkyl, by carboxyl groups, carboxyl groups esterified with $C_1$–$C_6$ -alkanols, trifluoromethyl groups, hydroxyl groups, methoxy groups, ethoxy groups, benzyloxy groups or by a benzyl group which is mono- or polysubstituted in the phenyl moiety by ($C_1$–$C_6$)-alkyl groups, halogen atoms or trifluoromethyl groups, or R is a benzyloxycarbonyl group or a tertiary-butoxycarbonyl radical (BOC radical), or an acetyl group, $R_1$ is a pyridine structure of formula 2

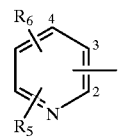

or its N-oxide, where the pyridine structure is alternatively bonded to the ring carbon atoms 2, 3 and 4 and is optionally substituted by the substituents $R_5$ and $R_6$; $R_5$ and $R_6$ are identical or different and signify ($C_1$–$C_6$)-alkyl, ($C_3$–$C_7$)-cycloalkyl, ($C_1$–$C_6$)-alkoxy, nitro, amino, hydroxyl, halogen, trifluoromethyl, ethoxycarbonylamino radical, and a carboxylkyloxy group in which the alkyl group has 1–4 C atoms;

$R_2$ is hydrogen or a ($C_1$–$C_6$)-alkyl group, where the alkyl group is mono- or polysubstituted by halogen and phenyl, which for its part is optionally mono or polysubstituted by halogen, ($C_1$–$C_6$)-alkyl, ($C_3$–$C_7$)-cycloalkyl, carboxyl groups, carboxyl groups esterified with $C_1$–$C_6$-alkanols, trifluoromethyl groups, hydroxyl groups, methoxy groups, ethoxy groups or benzyloxy groups, the ($C_1$–$C_6$)-alkyl group is optionally substituted by the 2-quinolyl group and the 2-, 3- and 4pyriddyl structure, which are optionally in each case mono- or polysubstituted by halogen, ($C_1$–$C_4$)-alkyl groups or ($C_1$–$C_4$)-alkoxy groups, or $R_2$ is an aroyl radical, where the aryl moiety on which the radical is based is a phenyl ring, which is optionally mono- or polysubstituted by halogen, ($C_1$–$C_6$)-alkyl, ($C_3$–$C_7$)-cycloalkyl, carboxyl groups, carboxyl groups esterified with $C_1$–$C_6$-alkanols, trifluoromethyl groups, hydroxyl groups, methoxy groups, epoxy groups or benzyloxy groups;

$R_3$ and $R_4$ are identical or different and are hydrogen, ($C_1$–$C_6$)-alkyl, ($C_3$–$C_7$)-cycloalkyl, ($C_1$–$C_6$)-alkanoyl, ($C_1$–$C_6$)-alkoxy, halogen and benzyloxy, or a nitro group, an amino group, a ($C_1$–$C_4$)-mono or diaklyl-substituted amino group, or a ($C_1$–$C_6$) alkoxycarbonylamino function or ($C_1$–$C_6$)-alkoxycarbonylamino-($C_1$–$C_6$)-alkyl function; and Z is O or S;

and their physiologically tolerable acid addition salts for the treatment of tumors or oncoses, said method comprising administering at least one of the following compounds or a physiologically acceptable acid addition salt or N-oxide thereof:

N-(pyridin-4-yl)-[1-(4-fluorobenzyl)-indol-3-yl] glyoxylamide;

N-(pyridin-4-yl)-(1-benzylindol-3-yl)-glyoxylamide;

N-(4-fluorophenyl)-[1-(3-pyridylmethyl)-indol-3-yl] glyoxylamide;

N-(pyridin-4-yl)-[1-(4-chlorobenzyl)-indol-3-yl] glyoxylamide; and

N-(pyridin-4-yl)-[1-(4-fluorobenzyl)-indol-3-yl] glyoxylamide hydrochloride salt;

a subject in need of such treatment.

* * * * *